(12) United States Patent
Bjornson et al.

(10) Patent No.: US 7,479,391 B2
(45) Date of Patent: Jan. 20, 2009

(54) PIPETTING APPARATUS WITH INTEGRATED LIQUID LEVEL AND/OR GAS BUBBLE DETECTION

(75) Inventors: Torleif Ove Bjornson, Gilroy, CA (US); Robert Liebhard, Zurich (CH); Adi Zuppiger, Siebnen (CH); Dirk Heerklotz, Stafa (CH)

(73) Assignee: Tecan Trading AG, Mannedorf (CH)

( * ) Notice: Subject to any disclaimer, the term of this patent is extended or adjusted under 35 U.S.C. 154(b) by 843 days.

(21) Appl. No.: 11/009,247

(22) Filed: Dec. 10, 2004

(65) Prior Publication Data

US 2006/0127281 A1    Jun. 15, 2006

(51) Int. Cl.
*B01L 3/02* (2006.01)

(52) U.S. Cl. .................. 436/54; 73/290 R; 73/712; 73/864.24; 73/865.9; 422/100; 422/922; 436/180

(58) Field of Classification Search ........... 73/31.04, 73/700, 712, 714, 744, 745, 865.9, 866.5, 73/863.01, 863.83, 863.86, 864, 34, 864.35, 73/290 R, 864.24, 864.25; 422/63–67, 100, 422/104, 105, 112, 115, 922, 929; 436/49, 436/54, 174, 180
See application file for complete search history.

(56) References Cited

U.S. PATENT DOCUMENTS

| | | | | |
|---|---|---|---|---|
| 3,894,438 | A | * 7/1975 | Ginsberg | ............... 73/863.01 |
| 4,675,301 | A | 6/1987 | Charneski et al. | |
| 4,794,085 | A | 12/1988 | Jessop et al. | |
| 5,499,545 | A | * 3/1996 | Kimura et al. | ........... 73/864.18 |
| 5,638,986 | A | 6/1997 | Tuominen et al. | |
| 5,723,795 | A | 3/1998 | Merriam et al. | |
| 7,097,623 | B2 | * 8/2006 | Colin et al. | .............. 600/579 |
| 2001/0047692 | A1 | * 12/2001 | Lipscomb et al. | ........ 73/864.25 |
| 2004/0020938 | A1 | 2/2004 | Boillat et al. | |
| 2004/0048393 | A1 | 3/2004 | Bruno et al. | |

FOREIGN PATENT DOCUMENTS

| | | |
|---|---|---|
| DE | 4447378 | 6/2005 |
| EP | 0571100 | 6/2005 |

* cited by examiner

*Primary Examiner*—Joseph W Drodge
(74) *Attorney, Agent, or Firm*—Notaro & Michalos P.C.

(57) ABSTRACT

A pipetting apparatus (1) comprises a fluidic space (7), to which a pressure transducer (11) with a pressure sensor (12) is attached with a gas filled space (15). The fluidic space (7) is defined by a pipette tip (2), a first tubing (5) that connects the pipette tip (2) to a pump (4), and an active part (6) of the pump (4). The pipetting apparatus (1) according to the present invention is characterized in that the pipetting apparatus (1) further comprises an impulse generating means (16, 18, 19) that is in operative contact with a column (10) of system liquid (8) inside the fluidic space (7). The impulse generating means (16, 18, 19) is designed to induce a vertical movement in this system liquid column (10), which results in a pressure variation in the gas filled space (15) that is pneumatically connected with the fluidic space (7). This pressure variation—as recorded with the pressure transducer (11) and as processed by a first data processing unit (13) during utilization of this pipetting apparatus—is taken as an indicator for the detection of penetration or of quitting of a surface (17) of a liquid, with an orifice (3) of the pipette tip (2), of which liquid an amount is to be aspirated and dispensed. This pressure variation is also taken as an indicator for the detection of the presence or the absence of gas bubbles in the system liquid (8) contained in the fluidic space (7) of this pipetting apparatus.

12 Claims, 5 Drawing Sheets

Fig. 1
Fig. 2
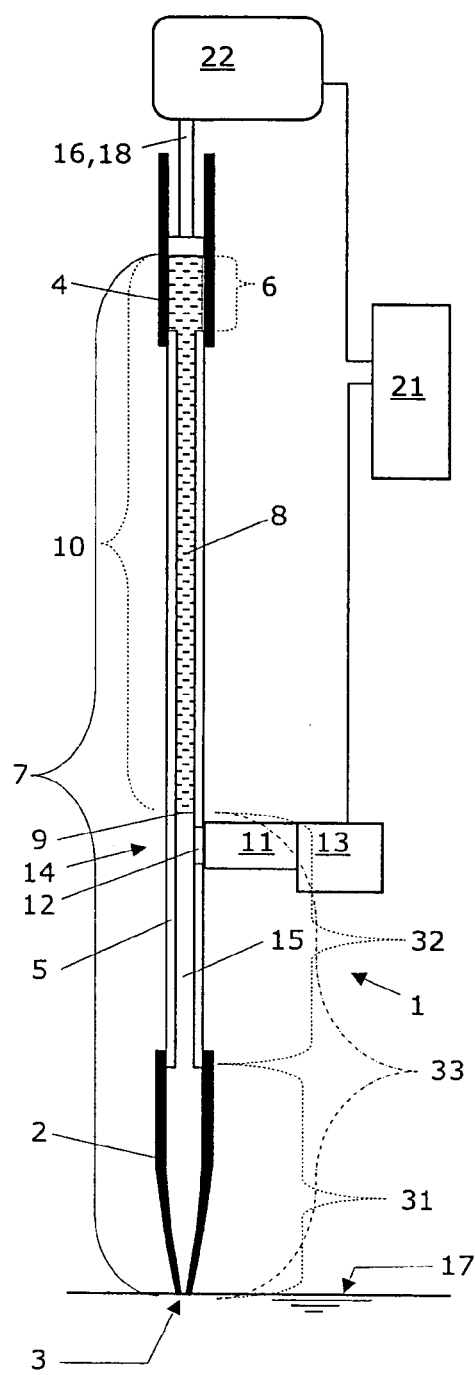
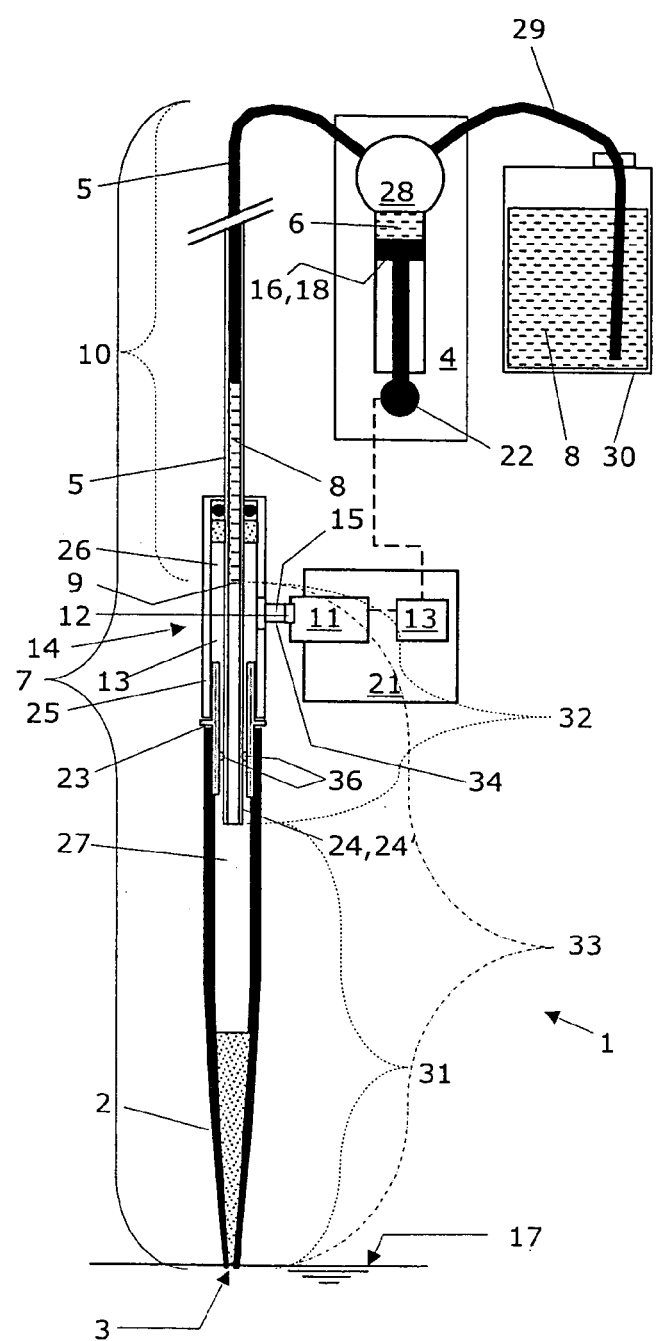

Fig. 3
Fig. 4
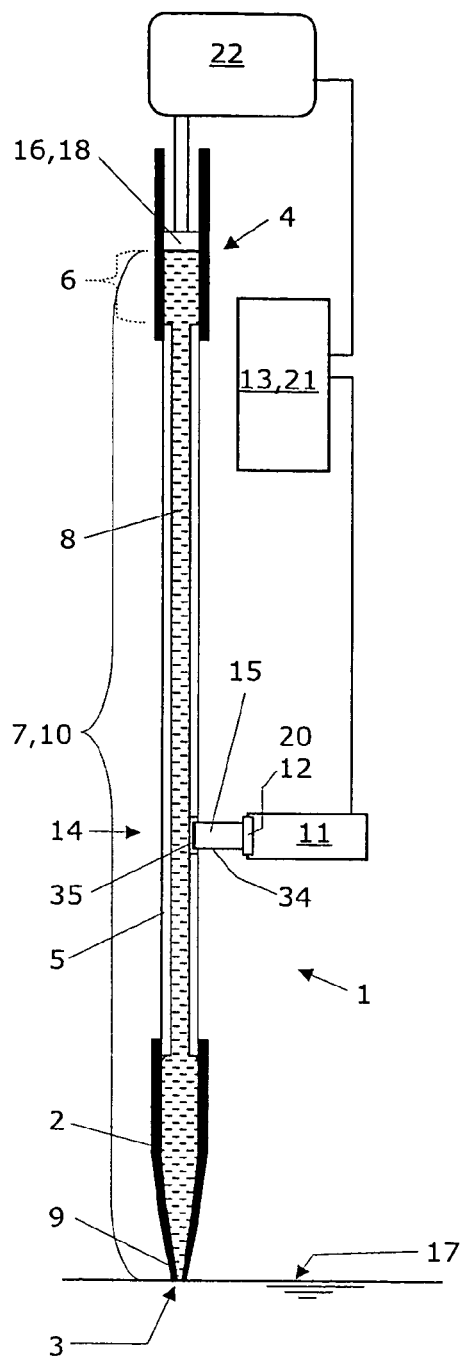
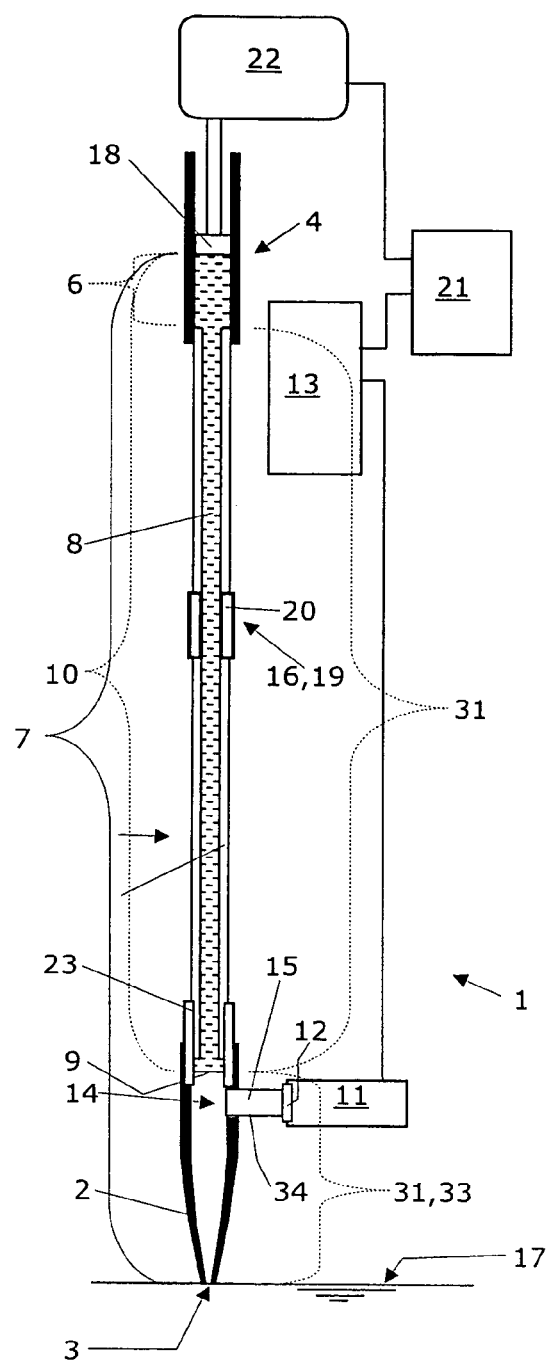

PIPETTING APPARATUS WITH INTEGRATED LIQUID LEVEL AND/OR GAS BUBBLE DETECTION

RELATED FIELD OF TECHNOLOGY

The present invention relates to a pipetting apparatus for the aspiration (or uptake) and dispensation (or delivering) of volumes of liquids, such as liquid samples. A pipetting apparatus of this type comprises a pipette tip with a pipette orifice and a pump. The pipette tip usually is connected to the pump by a first tubing. An active part of the pump, the first tubing and the pipette tip are defining a fluidic space. This fluidic space is at least partially filled with a system liquid, such that a meniscus is formed in the fluidic space at an end of a substantially continuous system liquid column. The typical pipetting apparatus further comprises a pressure transducer with a pressure sensor and a first data processing unit that is designed to process the data received from the pressure transducer. The pressure transducer is connected to the fluidic space via a connection site. The present invention also relates to a method of detecting the surface level of a liquid of which an amount is to be pipetted with such a pipetting apparatus. In addition, the present invention relates to a method of detecting the presence of gas bubbles in the system liquid of such a pipetting apparatus.

RELATED PRIOR ART

Industries applying biochemical techniques in e.g., pharmaceutical research and clinical diagnostics require systems for the handling of liquid volumes or liquid samples. Automated systems usually comprise one or more pipetting apparatus operating on liquid containers situated on a worktable. Such systems often are capable to perform operations on these liquids or samples, such as optical measurements, pipetting, washing, centrifugation, incubation, and filtration. One or more robots, such as Cartesian or polar style robots, may be used for operating on such a worktable surface. These robots can carry liquid containers, such as sample tubes or microplates. Robots can also be implemented as robotic sample processors (RSP) such as a pipetter for aspirating and dispensing liquids or as a dispenser for delivering of liquids. A central control system or computer usually controls these systems. The primary advantage of such a system is complete hands free operation. Accordingly, these systems can run for hours or days at a time with no human intervention.

From U.S. Pat. Nos 4,675,301 and 4,794,085 as well as U.S. Pat. No. 5,723,795 a typical pipetting apparatus with a motor driven pump and a pipette tip with a pipette orifice is known. The pipette tip is connected to the pump by tubing. This pipetting apparatus further comprises a pressure transducer that is fluidly connected to the tubing at a site of connection. The motor drive of the pump and the pressure transducer are electrically connected to a data processing unit that monitors the drive of the pump and that processes the data received from the pressure transducer. In U.S. Pat. Nos. 4,675,301 and 4,794,085, the pump, the tubing and the pipette tip are reported to be completely filled with a gas. One of the drawbacks of this approach lays in the compressibility of gases, which badly influences or even compromises sensitive and precise detection of pressure changes.

The same fluidic space may be completely filled with a system liquid according to U.S. Pat. No. 5,723,795. Drawbacks of this approach include a possible covering of the pressure sensor with components of the system liquid. In addition, moving the liquid-filled tubing (e.g., when the robot moves the pipette tip down towards the fluid surface at a desired pipetting position) will create spurious pressure signals due to the inertia of the liquid within the tubing. These signals can be large enough to render the pressure sensor signal unusable during movement, and may require a pause after movement to allow the spurious signal to dissipate before a usable signal is available again. Further, it is to be noted that the system fluid hydraulically couples any mechanical noise or vibrations from the mechanism and structure directly into the sensor.

OBJECTS AND SUMMARY OF THE INVENTION

A first object of the present invention is therefore to suggest an alternative pipetting apparatus for the aspiration and dispensation of volumes of liquids.

A second object of the present invention is to suggest an alternative method of detecting the surface level of a liquid, of which an amount is to be pipetted with a pipetting apparatus.

A third object of the present invention is to suggest an alternative method of detecting the presence of gas bubbles in the system liquid of a pipetting apparatus.

These and even further objects are achieved with the features of the independent claims attached. Advantageous refinements and additional features of the present invention result from the dependent claims.

The first object is achieved by the provision of a pipetting apparatus, comprising a pipette tip with a pipette orifice and a pump. The pipette tip is connected to the pump by a first tubing. An active part of the pump, the first tubing and the pipette tip are defining a fluidic space that is at least partially filled with a system liquid, such that a meniscus is formed in the fluidic space at an end of a substantially continuous system liquid column. The pipetting apparatus further comprises a pressure transducer with a pressure sensor and preferably also a data processing unit, designed to process the data received from the pressure transducer.

The pressure transducer is connected to the fluidic space via a connection site. The pipetting apparatus according to the present invention is characterized in that the pipetting apparatus 1 further comprises an impulse generating means that is in operative contact with a column of system liquid inside the fluidic space. The impulse generating means is designed to induce a vertical movement in this system liquid column, which results in a pressure variation in the gas filled space that is pneumatically connected with the fluidic space.

In a first preferred embodiment of the pipetting apparatus, the pressure variation —as recorded with the pressure transducer and as processed by the first data processing unit—is indicative for the penetration or quitting of a liquid surface with the pipette orifice.

In a second preferred embodiment of the pipetting apparatus, the pressure variation—as recorded with the pressure transducer and as processed by the first data processing unit—is indicative for the presence or absence of gas bubbles in the system liquid contained in the fluidic space.

The second object is achieved by the provision of a method of detecting the surface level of a liquid of which an amount is to be pipetted, which method is carried out with a pipetting apparatus according to the first preferred embodiment. The method according to the invention comprises the steps of:
 (a) Filling the fluidic space (7) at least partially with a system liquid (8) and forming a substantially continuous system liquid column (10) within the fluidic space (7);
 (b) Inducing a vertical movement in this system liquid column (10) by an impulse generating means (16, 18,

19) that is in operative contact with the system liquid column (10), thereby causing a pressure variation in the gas filled space (15) that is pneumatically connected with the fluidic space (7);

(c) Recording the pressure variation in the gas filled space (15) with the pressure transducer (11) and processing the recorded data with a first data processing unit (13); and (d) Deciding according to the processed data, whether a liquid surface (17) had been penetrated or quitted with an orifice (3) of the pipette tip (2).

The third object is achieved by the provision of a method of detecting the presence of gas bubbles in the system liquid of a pipetting apparatus, which method is carried out with a pipetting apparatus according to the second preferred embodiment. The method according to the invention comprises the steps of:

(a) Filling the fluidic space at least partially with a system liquid and forming a substantially continuous system liquid column within the fluidic space;

(b) Inducing a vertical movement in this system liquid column by an impulse generating means that is in operative contact with the system liquid column, thereby causing a pressure variation in the gas filled space that is pneumatically connected with the fluidic space;

(c) Recording the pressure variation in the gas filled space with the pressure transducer and processing the recorded data with a first data processing unit; and (d) Deciding according to the processed data, whether gas bubbles are present in the system liquid that is within the fluidic space.

ADVANTAGES PROVIDED BY THE INVENTION

Advantages of the present invention comprise:

The active part (e.g., the piston) of the pump for moving the system liquid is in direct contact with the in-compressible system liquid column. Thus, the working surface of the pump is displaced from the pump into the tubing or pipette tip, e.g., close to the pressure transducer.

The sensor of the pressure transducer is dry and free of any deposits originating from the system liquid.

Hydraulic transmission of mechanical vibration from the system to the pressure sensor is limited due to the damping effect of the gas filled space in front of the pressure sensor.

Even abrupt movements of a pipetting robot that comprises such an apparatus according to the invention are not disturbing the sensor signal of the pressure transducer, because the gas in the gas filled space acts as a damper. Thus spurious pressure signals caused from system fluid inertia while robot is moving are eliminated.

The gas space in the vicinity of the pressure transducer may be very small, thus, a minimum of a compressible medium is separating the system liquid from the sample liquid to be pipetted.

Liquid level detection (LLD) on electrically conductive as well as on nonconductive liquids can be carried out.

The simultaneous addition of the LLD according to the invention to other LLD techniques, such as capacitive LLD, increases the safety of the liquid level detection.

A pipetting apparatus according to the present invention has (unlike e.g., capacitive or conductive techniques) the ability to discriminate between gas-filled bubbles and a true liquid meniscus.

BRIEF DESCRIPTION OF THE DRAWINGS

The device according to the present invention and/or the methods according to the present invention will be described in greater detail on the basis of schematic and exemplary drawings, without these drawings restricting the scope of the present invention. It is shown in:

FIG. 1 a vertical section of a first variant of the pipetting apparatus with the meniscus located in the tubing;

FIG. 2 a vertical section of a second variant of the pipetting apparatus with the meniscus located in the tubing;

FIG. 3 a vertical section of a third variant of the pipetting apparatus with the meniscus located in the pipette tip;

FIG. 4 a vertical section of a fourth variant of the pipetting apparatus with the meniscus located in the pipette tip;

FIG. 6A shows a continuous bidirectional oscillation movement;

FIG. 6B shows a discontinuous bidirectional oscillation movement;

FIG. 6C single bidirectional pulse movement;

FIG. 6D repeated bidirectional pulse movement;

FIG. 6E single unidirectional downward step movement;

FIG. 6F single unidirectional upward step movement;

FIG. 6G repeated unidirectional downward step movement;

FIG. 6H repeated unidirectional upward step movement;

FIG. 7 a vertical section of a piston type pump with a piezo actuator at the active surface of the piston:

FIG. 8 a vertical section of a piston type pump with a piezo actuator that is part of the tubing:

FIG. 9 partial sections through alternative impulse generating means that are independent of a pump, whereas:

FIG. 15 system oscillations, preferably as produced with a electrically controlled impulse generation means, are correlated with:

DETAILED DESCRIPTION OF THE INVENTION

Figure 5:
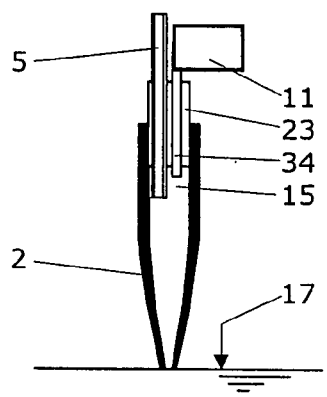
FIG. 5 an alternative to the first variant of FIG. 1.

FIG. 1 shows a vertical section of a first variant of the pipetting apparatus with the meniscus located in the tubing. This pipetting apparatus 1 comprises a pipette tip 2 with a pipette orifice 3 and a pump 4. Conventional pipette tips can be used as one-way disposable tips or as reusable tips as they are known per se. The pump can be a piston pump like the "CAVRO XP3000 plus Modular Digital Pump" (Tecan Systems Inc., 2450 Zanker Road, San José, Calif. 95138, USA) or a bellows pump as likewise known from U.S. Pat. No. 5,638,986.

The pipette tip 2 is connected to the pump 4 by a first tubing 5. An active part 6 of the pump 4, which preferably is embodied as a piston or a bellow, the first tubing 5 and the pipette tip 2 define a fluidic space 7 that is at least partially filled with a system liquid 8. This filling with system liquid is such that a meniscus 9 is formed in the fluidic space 7 at an end of a substantially continuous system liquid column 10. In FIG. 1, the meniscus 9 is shown to be in the first tubing 5 and outside of the pipette tip 2.

The pipetting apparatus 1 further comprises a pressure transducer 11 with a pressure sensor 12 and preferably also comprises a first data processing unit 13. The data processing unit 13 is designed to process the data received from the pressure transducer 11.

The pressure transducer 11 is connected to the fluidic space 7 via a connection site 14. This connection site 14 comprises a gas filled space 15, which is pneumatically connected with the fluidic space 7. The pressure sensor 12 limits the gas filled space 15, because here, the pressure sensor 12 is essentially in line with the first tubing 5. The gas filled space 15 preferably is filled with air or with a chemically inert gas like $N_2$.

The pipetting apparatus 1 further comprises an impulse generating means 16, 18, 19 that preferably is electrically controlled and in operative contact with the system liquid column 10 inside the fluidic space 7 and that is designed to induce a vertical movement in this system liquid column 10, which results in a pressure variation in the gas filled space 15.

There are two major applications for taking advantage of the pressure variation in the gas filled space 15:

(A) The pressure variation—as recorded with the pressure transducer 11 and as processed by the first data processing unit 13—is indicative for the penetration or quitting of a liquid surface 17 with the pipette orifice 3. Thus, the detection and interpretation of the pressure variation in the gas filled space 15 is utilized for detection of a surface of a liquid to be pipetted. This pressure monitored liquid level detection (pLLD) is independent from the electric conductivity of the liquid that is to be aspirated and dispensed.

(B) The pressure variation—as recorded with the pressure transducer 11 and as processed by the first data processing unit 13—is indicative for the presence or absence of gas bubbles in the system liquid 8 contained in the fluidic space 7.

Such inducing of reciprocal movement is now discussed in view of the first major application of the pressure variation in the gas filled space 15, the detection of a liquid level 17 of a liquid to be pipetted. In the context of the present invention, the terms "liquid level 17", "liquid surface", and "phase border between a liquid (sample or other liquid) and the surrounding atmosphere" is treated and understood as synonyms.

As can be seen in FIG. 1 depicting the first variant of the pipetting apparatus, the meniscus 9 of the system liquid column 10 preferably is located inside the first tubing 5. In this case, the gas filled space 15 is a substantial part 31 of the pipette tip 2 volume and a substantial part 32 of the tube 5 volume. In this variant, the connection site 14 may be located in a wall of the pipette tip 2 (see FIG. 4) or in a wall of the first tubing 5 (see FIG. 1). Here, the connection site 14 is located between the pipette orifice 3 and the meniscus 9 and the pressure transducer 11 is directly attached to the connection site 14, which is open to a part 33 of the fluidic space 7 that is filled with gas. The pipette tip 2 is one selected from a group comprising, e.g., disposable single pipette tips and disposable multiple pipette tips as well as single and multiple pipetting needles.

The advantage of this first embodiment lays in its simple construction, which enables the parallel alignment of a larger number (e.g., 8 or 12) of such pipetters in a robotized sample processing unit (not shown) for example. If only one pipetter channel is fitted to a robot arm (not shown), it may be sufficient to process the data recorded with the pressure transducer 11 by the first data processing unit 13. Control of the drive 22 of the pump may be carried out manually.

If, however an automated pipetter or even a multitude of such automated pipetters are aligned on a robot arm of a laboratory work station (not shown), it is preferred that a second data processing unit 21 is connected to the motor drive 22 of the pump 4 and to the first data processing unit 13 in order to monitor this motor drive 22 according to the pressure variation in the gas filled space 15, as recorded by the pressure transducer 11 and processed by the first data processing unit 13. All pipetters can be controlled with the second data processing unit 21, which may be the central computer of a laboratory workstation.

FIG. 2 shows a vertical section of a second variant of the pipetting apparatus with the meniscus located in the tubing. In contrast to the first variant of FIG. 1, the first tubing 5 here comprises an adapter 23 for disposable pipette tips. The first tubing 5 also comprises an inner tubing 24 and an outer tubing 25. The outer tubing 25 comprises the connection site 14. The inner and outer tubing extend coaxially to each other and define a first coaxial gas space 26 between them. This first coaxial gas space 26 is pneumatically connected to a second coaxial gas space 27 located in a disposable pipette tip fixed to the adapter 23.

The advantage of this second embodiment lays in its complete separation of system liquid 8 and sample liquid inside the pipette tip 2. With this preferred construction, mixing of system liquid and sample liquid is avoided. Also here it is preferred that a second data processing unit 21 is connected to the motor drive 22 of the pump 4 and to the first data processing unit 13 in order to monitor this motor drive 22 according to the pressure variation in the gas filled space 15, as recorded by the pressure transducer 11 and processed by the first data processing unit 13. All pipetter channels can be individually controlled with the second data processing unit 21, which is integrated in each individual pipetter. The central computer of a laboratory workstation may achieve the synchronization of all pipetter channels.

The inner tubing 24 may be accomplished in a first embodiment as a continuous tubing constituted of one single plastic piece of the first tubing 5 that reaches from the pump 4 to the second coaxial gas space 27. This embodiment has the advantage of simple construction and of absolutely smooth surfaces along the whole first tubing 5. However, the diameter of such first tubing is to be kept relatively small, in order to reduce flexibility of the tubing. In a second embodiment, the inner tubing 24 may be accomplished as an inelastic, stiff tubing 5' that is connected to the first tubing 5, which leads to the pump 4. The inner tubing 24' directly reaches to the second coaxial gas space 27.

In both cases, it is preferred that the adapter 23 for disposable pipette tips comprises at least three distance guides 36 on the inner side, these distance guides 36 fix the central position of the inner tube 24, 24' coaxial to the outer tube 25.

These distance guides 36 are spaced from each other so that gas (and therefore also pressure variations in the gas) can easily pass from the first coaxial gas space 26 to the second coaxial gas space 27.

In order to also serve as a dispenser for volumes larger than a pipette tip volume (particularly when using fixed tips), the pipetting apparatus 1 in FIG. 2 comprises a pump 4 with a three-way valve 28, from which the first tubing 5 is leading towards the pipette tip 2 and a second tubing 29, which is leading to a liquid container 30. With this arrangement, large numbers of volumes of the sample liquid stored in the liquid container 30 can be pumped into the first tubing 5 and delivered at the appropriate positions with the pipetting apparatus 1. Also in this case, where the pipetting apparatus 1 is entirely used as a dispenser, there is no possible contact of the connection site 14 and the liquid to be dispensed. Thus, pressure monitoring with the pressure transducer 11 is guaranteed. In order to achieve easier attachment of the pressure transducer 11 to the outer tube 25, an additional tube 34 containing the gas filled space 15 connects the sensor 12 to the connection site 14.

As shown in FIG. 2, the liquid container 30 can also be utilized for storage of system liquid 8. Thus, the entire tubing 5, 29 and pipette tips 2 can be flushed with system liquid 8 via the three-way valve 28.

FIG. 3 shows a vertical section of a third variant of the pipetting apparatus with the meniscus located in the pipette tip. This variant is characterized in that the gas filled space 15 is defined as a volume in an additional tube 34 that connects the sensor 12 to the connection site 14 and that is sealed from the fluidic space 7 by a flexible membrane 35. According to this layout of pipetting apparatus 1, the entire fluidic space 7 can be filled with a substantially continuous system liquid column 10. The pressure sensor 12 cannot be covered with components of the system liquid 8, because the gas filled space 15 keeps the pressure sensor 12 dry. This gas filled space 15 can be of minimal extension so that merely a thin gap lays between the flexible membrane 35 and the pressure sensor 12. With this pipetting apparatus 1, a certain volume of sample liquid can be aspirated from a sample liquid container. Such container can be any kind of labware, like sample tubes, wells of microplates, troughs etc. Aspiration can be performed with or without an air gap between the system liquid 8 and the sample liquid.

FIG. 4 shows a vertical section of a fourth variant of the pipetting apparatus with the meniscus located in the pipette tip. This pipetting apparatus 1 is similar to the one according to first variant (see FIG. 1). However, there are characteristic differences between these variants as seen from FIG. 4:

(1) There is an adapter 23 for disposable pipette tips connecting the pipette tip 2 to the first tubing 5.

(2) The connection site 14 is not situated in the tubing 5, it may be placed in the pipette tip 2 (as shown) or in the adapter 23 (not shown).

(3) The pressure transducer 11 with its pressure sensor 12 are connected to the gas filled substantial part of the pipette volume by an additional tube 34 that comprises gas filled space 15.

(4) A constriction element 19 is integrated into the first tubing 5. This constriction element 19 may be present as a part of tubing 5 (see FIGS. 4 and 8B) or it may be placed on the outside of tubing 5 (see FIG. 9A), having an intimate contact to the tubing 5. This constriction element is the electrically controlled impulse generating means 16 that preferably is accomplished here as a piezo actuator 20 in form of tube.

It is expressly noted here that the preferably electrically controlled impulse generating means 16 not necessarily have to be physically connected with the pump 4 as it derives from element (4) above. However, synchronization of the impulse generating means 16 with the pump actions is preferred.

An alternative solution of the attachment of the pressure transducer 11 to the pipette tip, when compared with the first variant of FIG. 1 or with the fourth variant in FIG. 4, is seen in FIG. 5. The adapter 23 for disposable pipette tips connects the pipette tip 2 to the first tubing 5 in that the first tubing 5 is penetrating the adapter 23. In addition, an additional tube 34 also penetrates the adapter 23, which is accomplished as sealing plug. The pressure transducer 11 with its pressure sensor 12 is connected to the additional tube 34. The meniscus 9 (not shown) of the system liquid 8 is located within the first tubing 5, thus, the pipette tip is serving as the gas filled space 15, which is extended by the additional tube 34, and which is limited by the pressure sensor 12 and the orifice 3 of an empty pipette tip 2 that touches a surface 17 of a sample liquid to be pipetted. Like in FIG. 1, there is no membrane situated between the pressure sensor 12 and the sample or system liquid. Like in FIGS. 3 and 4, the pressure transducer is accomplished as an integrated circuit chip combined with the pressure sensor 12; thus, minimal construction volume is needed outside the first tubing 5, which is favorable for the preferred construction of a multi pipetter liquid handling system that comprises at least one pipetting apparatus 1 as shown in one of the FIGS. 1 to 5. It is preferred that such a multi pipetter comprises 8 or 12 of these pipetting apparatuses 1. Such a liquid handling system preferably further comprises a liquid handling robot and a control unit (not shown).

There are many possible ways of inducing a pressure variation in the gas filled space 15 of a pipetting apparatus 1 according to the present invention. Simple embodiments comprise vibrating Z-drives of a liquid handling workstation. These vertical vibrations oscillate the column 10 of system liquid 8 inside the first tubing 5, which results in the desired pressure variation or pressure oscillation in the gas filled space 15 in front of the pressure sensor 12. Also knocking against the tubing may induce a similar effect. Such embodiments have the advantage that no or only little changes are necessary in the movement controls for the vertical movement of the robotized pipetter arm in order to achieve the desired performance. However, such embodiments entail the drawback of lack of reproducibility (knocking) or such vibration movements with the Z-drive may compromise the lifetime of an apparatus and may also be recognized by the laboratory personnel.

Figure 6:
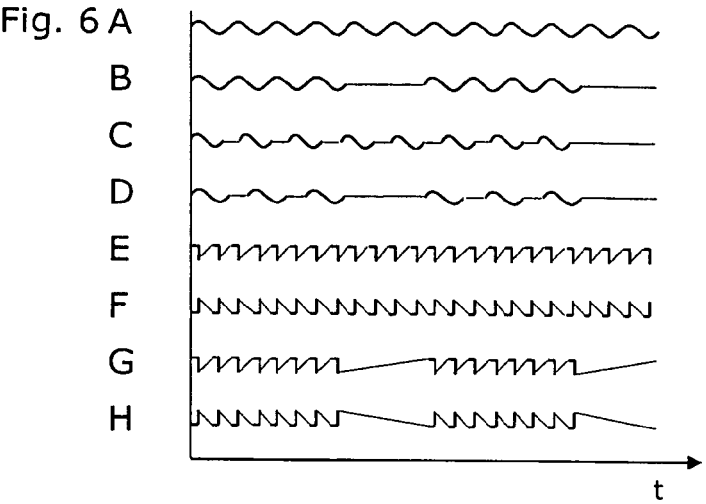
FIG. 6 a schematic presentation of selected vertical movements of the system liquid column within the fluidic space of the pipetting apparatus.

Dependent of how the pressure variation or pressure oscillation in the gas filled space 15 in front of the pressure sensor 12 is produced, there are many preferred pressure variations possible, a selection of which is depicted in FIG. 6. There, a schematic presentation of selected vertical movements of the system liquid column within the fluidic space of the pipetting apparatus is drawn in a time-based diagram. Such movements comprise a continuous (FIG. 6A) and a discontinuous (FIG. 6B) bidirectional oscillation movement. Both represent a pendulousness with a different multitude of oscillations. Such movements also comprise a single (FIG. 6C) and a repeated (FIG. 6D) bidirectional pulse movement. Both represent single pendulous oscillations. The series of which may be of different length. Possible ways of producing such pressure variations comprise the use of an active element that is able to reciprocally move the liquid column 10. Such active elements comprise a pump piston (see FIGS. 1-3), pump bellows (not shown), and constriction elements 19 (see FIG. 4). Additional reciprocally moving elements are shown in FIG. 9 below.

Such movements also comprise step-like unidirectional downward or upward movements of the liquid column 10 in form of a large number of single downward (FIG. 6E) or upward step movements (FIG. 6F). Such movements further comprise step-like unidirectional downward or upward movements of the liquid column 10 in form of series of small repeated numbers of single downward (FIG. 6G) or upward step movements (FIG. 6H). Possible ways of producing such pressure variations comprise the use of an active element that is able to unilaterally move the liquid column 10. Such active elements comprise a pump piston (18, see FIGS. 1-3) and pump bellows (not shown). Preferably, the steps are aspiration steps. Possible ways of producing such pressure variations comprise the application of triangular or saw-tooth wave shapes.

Any combinations of these movements are applicable too: In FIGS. 6E to 6H, e.g., the pressure variation can be produced in that advancing the liquid column is always followed by a retraction of the liquid column. However, advancing is carried out quick (vertical thick line in the graph) and retraction is carried out slowly (inclined thin line in the graph). Preferably, a short rest time (thick horizontal line in the graph) precedes every quick movement.

Figure 7A:
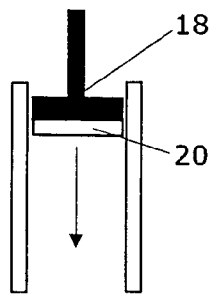
FIG. 7A Plunger movement.
Figure 7B:
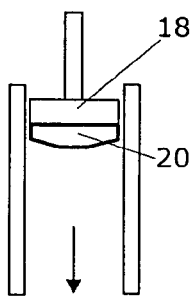
FIG. 7B Piezo movement.
Figure 8A:
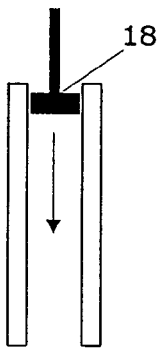
FIG. 8A Plunger movement.
Figure 8B:
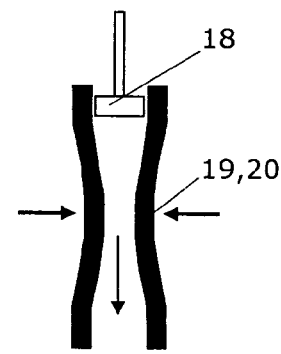
FIG. 8B Piezo movement.

Inducing a pressure variation in the gas filled space 15 of a pipetting apparatus 1 according to the present invention can be carried out by a piston (18) or by bellows of a pump. FIG. 7 shows a vertical section of a piston type pump with a piezo actuator 20 at the active surface of the piston 18. For aspiration or dispensation, the piston 18 can be moved conventionally (FIG. 7A). For inducing pressure variation in the gas filled space 15 of a pipetting apparatus 1, the active piezo membrane 20 is put into operation (FIG. 7B). FIG. 8 shows a vertical section of a piston type pump with a piezo actuator that is part of the tubing. For aspiration or dispensation, the piston 18 can be moved conventionally (FIG. 8A). For inducing pressure variation in the gas filled space 15 of a pipetting apparatus 1, the piezo tube 20 is put into constriction operation (FIG. 8B). The impulse generating means according to the FIGS. 7 and 8 are mainly applicable for reciprocal movements as depicted in FIGS. 6A-6D.

Figure 9A:
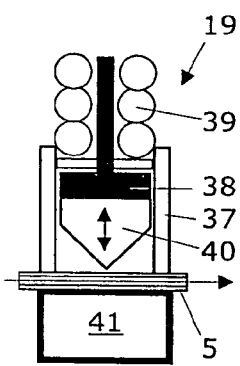
FIG. 9A shows an electro-mechanical variant.

FIG. 9 shows alternative impulse generating means that are independent of a pump and that can also be utilized for inducing a pressure variation in the gas filled space 15:

FIG. 9A shows an electro-mechanical variant. Fist tubing 5 is lead through a cylinder 37. Inside of the cylinder 37, a piston 38, driven by a solenoid 39 and carrying a wedge 40, is moved in essentially perpendicular direction against the closed surface of the first tubing 5. This movement reversibly deforms the first tubing 5. The preferred filling of the cylinder 37 is air. Preferably the wedge 40 is of resilient plastic material in order not to cut the tubing 5 when punching against it. A preferably rigid bottom 41 closes the cylinder on the side opposite to the piston 38. Instead of a wedge (40), also other geometries formed from solid-state material, like balls and flat or curved pistons can be utilized.

Figure 9B:
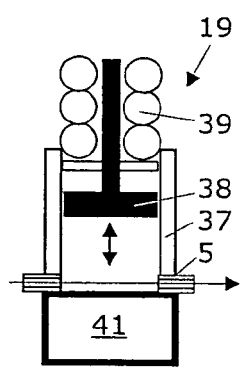
FIG. 9B shows a first hydraulic variant.

FIG. 9B shows a first hydraulic variant. Fist tubing 5 is lead through the walls of a cylinder 37. Inside of the cylinder 37, the first tubing 5 is cut open. The cylinder is filled with a liquid, like system liquid 8 (for a pipetter) or sample liquid (for a dispenser). A piston 38, driven by a solenoid 39, is moved in essentially perpendicular direction against the open part of the first tubing 5. This movement induces a pressure wave in the liquid of the cylinder 37 as well as in the liquid that is present in the tubing 5. A preferably rigid bottom 41 closes the cylinder on the side opposite to the piston 38.

Figure 9C:
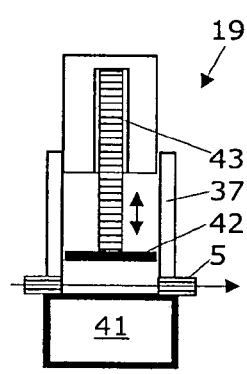
FIG. 9C shows a second hydraulic variant.

FIG. 9C shows a second hydraulic variant. Fist tubing 5 is lead through the walls of a cylinder 37. Inside of the cylinder 37, the first tubing 5 is cut open. The cylinder is filled with a liquid, like system liquid 8 (for a pipetter) or sample liquid (for a dispenser). A passive membrane 42 closes the cylinder 37 opposite to the bottom 41. It is driven by a piezo stack 43, which is moved in essentially perpendicular direction against the open part of the first tubing 5. This movement induces a pressure wave in the liquid of the cylinder 37 as well as in the liquid that is present in the tubing 5. The preferably rigid bottom 41 closes the cylinder on the side opposite to the membrane 42. The volume of the cylinder 37 preferably is larger than the volume of the cut away tubing 5. However, it may be considerably smaller than in the variants of FIGS. 9A and 9B. In an alternative variant (not shown), the membrane 42 is an active piezo membrane and the piezo stack is not present. The cylinder filling of the rear side of the membrane 42 preferably is air.

Figure 9D:
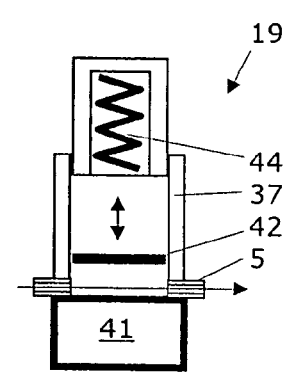
FIG. 9D shows a third hydraulic variant.

FIG. 9D shows a third hydraulic variant. Fist tubing 5 is lead through the walls of a cylinder 37. Inside of the cylinder 37, the first tubing 5 is cut open. The cylinder is filled with a liquid, like system liquid 8 (for a pipetter) or sample liquid (for a dispenser). A passive membrane 42 closes the cylinder 37 opposite to the bottom 41. The cylinder filling of the rear side of the membrane 42 preferably is air. The membrane 42 is driven by a driven by sudden expansion of the air when heated with the heater 44. Thus, the membrane 42 is partly moved in essentially perpendicular direction against the open part of the first tubing 5. This movement induces a pressure wave in the liquid of the cylinder 37 as well as in the liquid that is present in the tubing 5. A preferably rigid bottom 41 closes the cylinder on the side opposite to the piston 38. The volume of the cylinder 37 preferably is larger than the volume of the cut away tubing 5. However, it may be considerably smaller than in the variants of FIGS. 9A and 9B.

The impulse generating means according to the FIGS. 9A-9D are mainly applicable for reciprocal movements as depicted in FIGS. 6A-6D. These impulse generating means are regarded as constriction elements 19, which are a part of (see FIG. 9B-9D), or which are acting on (see FIG. 9A) the first tubing 5.

The method of detecting the surface 17 of a liquid of which an amount is to be pipetted according to the present invention is carried out with a pipetting apparatus 1. This pipetting apparatus 1 comprises a pipette tip 2 with a pipette orifice 3 and a pump 4. The pipette tip 2 is connected to the pump 4 by a first tubing 5.

An active part 6 of the pump 4, the tubing 5 and the pipette tip 2 define a fluidic space 7. The pipetting apparatus 1 further comprises a pressure transducer 11 with a pressure sensor 12 and preferably also a first data processing unit 13, designed to process the data received from the pressure transducer 11. The pressure transducer 11 is connected to the fluidic space 7 via a connection site 14. The connection site 14 comprises a gas filled space 15 that is pneumatically connected with the fluidic space 7 and that is limited by the pressure sensor 12. The gas filled space 15 preferably is filled with air or with a chemically inert gas like $N_2$. The pipetting apparatus 1 further comprises a preferably electrically controlled impulse generating means 16, 18, 19 that is in operative contact with the system liquid column 10 inside the fluidic space 7.

The inventive method comprises the following steps:
(a) Filling the fluidic space 7 at least partially with a system liquid 8 and forming a substantially continuous system liquid column 10 within the fluidic space 7;
(b) Inducing a vertical movement in this system liquid column 10 by an impulse generating means 16, 18, 19 that is in operative contact with the system liquid column 10, thereby causing a pressure variation in the gas filled space 15 that is pneumatically connected with the fluidic space 7;
(c) Recording the pressure variation in the gas filled space 15 with the pressure transducer 11 and processing the recorded data with a first data processing unit 13; and
(d) Deciding according to the processed data, whether a liquid surface 17 had been penetrated or quitted with an orifice 4 of the pipette tip 2.

This pressure monitored liquid level detection (pLLD) can be carried out by discontinuous oscillating, single pulsing, or single stepping this system liquid column 10 of step (b) in between of two steps of moving the pipette orifice 4 towards the liquid surface 17. This liquid level detection can also be carried out by continuous oscillating, repeated pulsing, or repeated stepping this system liquid column 10 of step (b) during movement of the pipette orifice 4 towards the liquid surface 17. Movement towards the liquid surface 17 can be carried out in order to penetrate or to quit the liquid level 17.

In a first experiment (see FIG. 10), erratic movement of the Z-rod of a robotic sample processor (RSP) was applied for pressure monitored liquid level detection (pLLD):

The channels II, IV, VI, and VIII of the RSP were equipped with pressure sensors 12, connected to a first data processing unit 13. In order to monitor and record the plunger or piston 18 movements of the dilutor pumps 4 of the respective channels II, IV, VI, and VIII, the pumps were additionally equipped with linear potentiometers. The Z-movement was carried out with a modified DC-Servo firmware that moves the Z-rod alternating with two different speeds. The scan rate of the data logger was 2000/sec.

The voltage indicated is measured at the gate of the signal amplifier of the pressure transducer 11. The voltage indicated in the FIGS. 10 to 14 can be converted into pressure differences, as 0.02 V are equal to 1 mbar.

The recorded process includes the steps of:
i) flushing of all adapters 23 for disposable pipette tips 2 with system liquid 8;
ii) aspiration of a trailing air gap of 10 µl;
iii) pick-up of disposable pipette tips 2 (200 µl, standard, filtered);
iv) movement of the RSP arm with four attached pipetting apparatuses 1 over a liquid container (trough);
v) start oscillation; and
vi) Z-movement towards the liquid surface 17.

Figure 10:
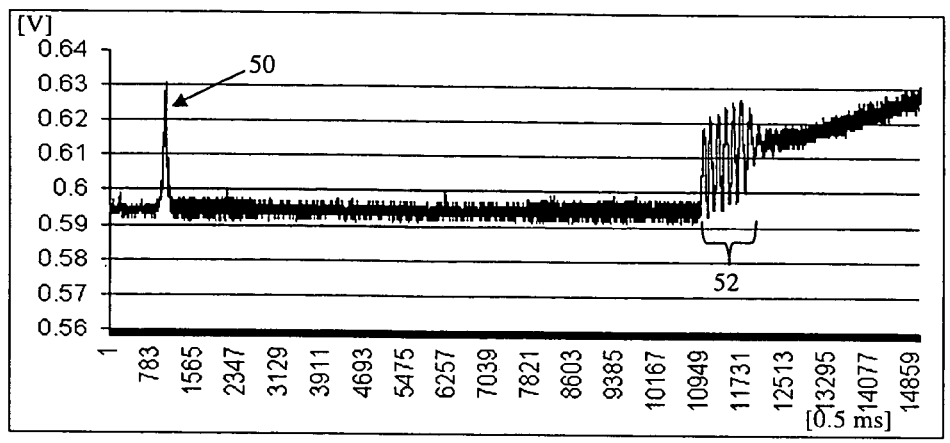
FIG. 10 erratic movement of the Z-rod of a robotic sample processor was applied for pressure monitored liquid level detection (pLLD)

The record is shown in FIG. 10, where picking up the disposable pipette tip 2 (50) and the detection of the liquid level 17 (52) is clearly visible.

Figure 11:
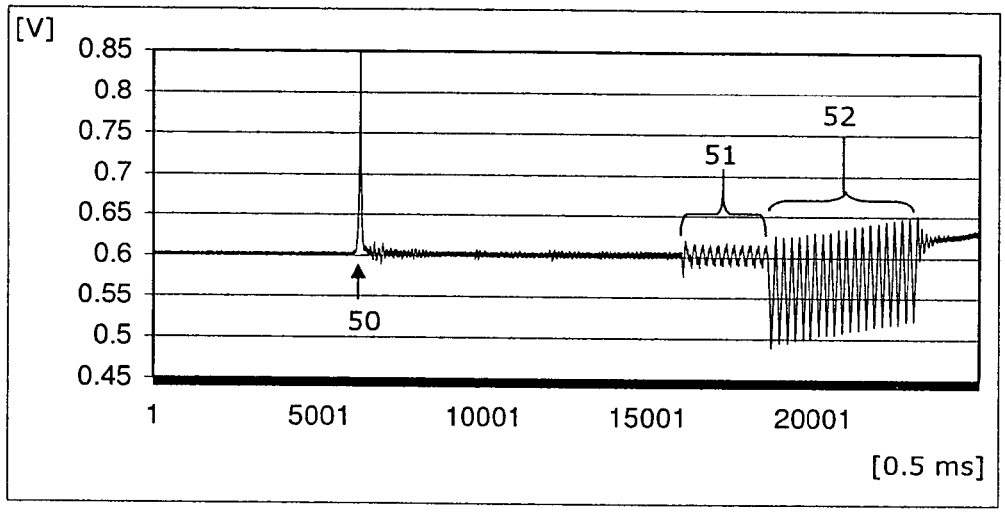
FIG. 11 oscillation movement of the pump piston of a pipetting apparatus was applied for pressure monitored liquid level detection (pLLD)

In a second experiment (see FIG. 11), oscillation movement of the pump piston 18 of a pipetting apparatus 1 was applied for pressure monitored liquid level detection (pLLD):

Equipment and process were the same as in the first experiment, except that a modified firmware was used for controlling the pump piston 18, Z-rod movement was standard. The record is shown in FIG. 11, where picking up the disposable pipette tip 2 (50), the detection of the oscillation with the pipette tip 2 in air (51), and the detection of the oscillation with the pipette tip penetrating liquid level 17 (52) is clearly visible. The different oscillation amplitudes help to distinguish between the actual positions (air/liquid) of the pipette tip. The piston movement is similar as discussed with FIG. 6A. The voltage indicated is measured at the gate of the signal amplifier of the pressure transducer 11. The actual movement of the pump piston 18 was +/−6 steps (out of a total of 3000 possible piston movement steps). Utilizing this pump piston oscillation with 1000 µl pipette tips 2, three steps are equal to a displacement volume of the system liquid column 10 of 1 µl. Thus, here the system liquid column oscillated by about +/−2 µl. The oscillation pressure measurements enable the discrimination whether pipette tips 2 with or without filter are utilized.

If a filtered pipette tip is attached, the pressure oscillation measurement (see FIG. 11) results in smaller amplitudes, which nevertheless are characteristic enough for pressure monitored liquid level detection.

In a third experiment (see FIG. 12), oscillation movement with a modified pinch valve, according to FIG. 9A was applied for pressure monitored liquid level detection (pLLD).

Figure 12:
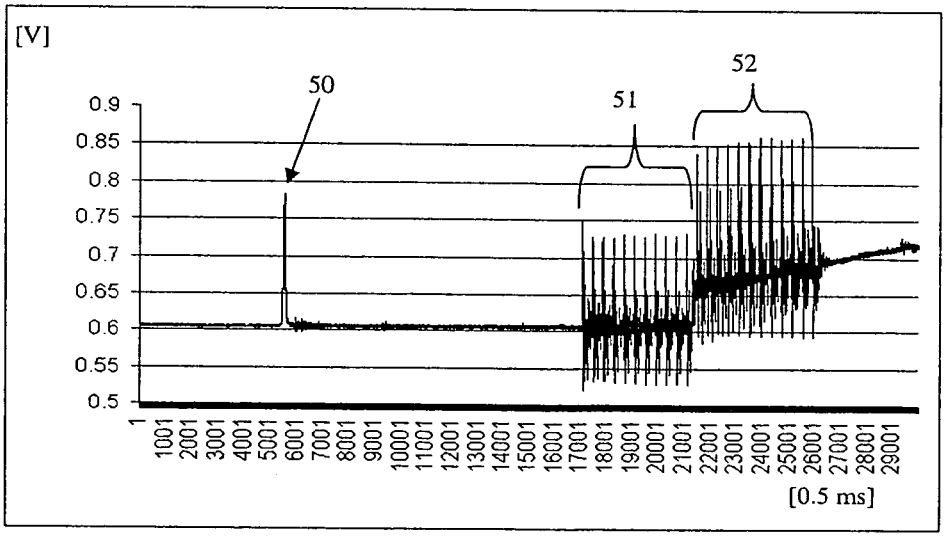
FIG. 12 oscillation movement with a modified pinch valve, according to FIG. 9A was applied for pressure monitored liquid level detection (pLLD)

Equipment and process were the same as in the second experiment, except that the firmware for controlling the pump piston 18 and the Z-rod movement was standard. Instead of oscillating the piston, the solenoid valve was oscillated with 5 Hz; a 1000 µl pipette tip 2 was used here. The record is shown in FIG. 12, where picking up the disposable pipette tip 2 (50), the detection of the oscillation with the pipette tip 2 in air (51), and the detection of the oscillation with the pipette tip penetrating liquid level 17 (52) is clearly visible. The different oscillation amplitude and characteristics help to distinguish between the actual positions (air/liquid) of the pipette tip. The piston movement is similar as discussed with FIG. 8A. Again a filtered pipette tip was attached. The actuation frequency of 5 Hz (5 strokes of the pinch valve per second) proved to be a good value for pLLD with a 1000 µl disposable pipette tip 2.

In a fourth experiment (see FIG. 13), pressure measurement in the gas filled space 15 of the pipetting apparatus 1 (pLLD) was applied in combination with capacitive liquid level detection (cLLD):

The channel II was equipped with a standard cLLD unit and the channel IV of the RSP was equipped with a pressure sensor 12 according to the present invention. In order to monitor and record the plunger or piston 18 movements of the dilutor pumps 4 of the respective channels II and IV, the pumps were additionally equipped with linear potentiometers. The movement of the Z-rod was carried out with a standard firmware. The pump piston 18 was driven for aspiration of liquid at a slow speed with a defined number of 200 steps per second. As before, the utilized piston pump was able to perform a total of 3000 piston movement steps. The scan rate of the data logger again was 2000/sec.

The recoded process includes the steps of:
i) flushing of all adapters 23 for disposable pipette tips 2 with system liquid 8;
ii) aspiration of a trailing air gap of 10 µl;
iii) pick-up of disposable pipette tips 2 (200 µl or 1000 µl, standard with or without filter);
iv) movement of the RSP arm with two attached pipetting apparatuses 1 over a liquid container (trough).

With the pipette tip 2 of channel II, capacitive LLD was performed twice in order to have a safe mode with double detection of the liquid level 17 with the pipette tip of channel II. The detected height or Z-level of the liquid surface 17 was stored in a second data processing unit 21 and the pipette tip of channel II, which was only used for cLLD here, was then retracted to a vertical Z-value for save traveling in horizontal X and Y directions.

Figure 13:
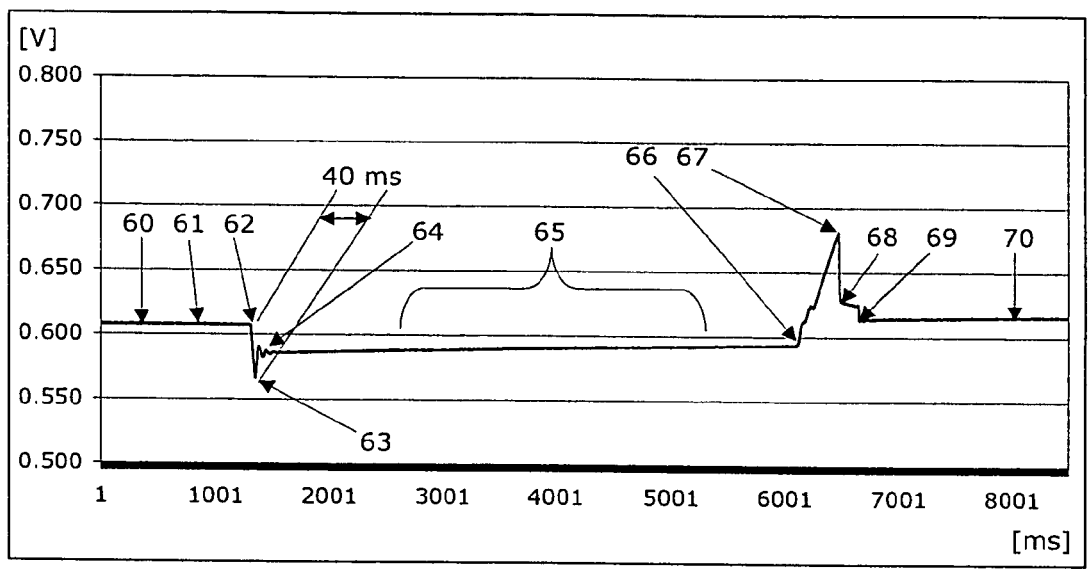
FIG. 13 pressure measurement in the gas filled space of the pipetting apparatus (pLLD) was applied in combination with capacitive liquid level detection (cLLD)
Figure 14:
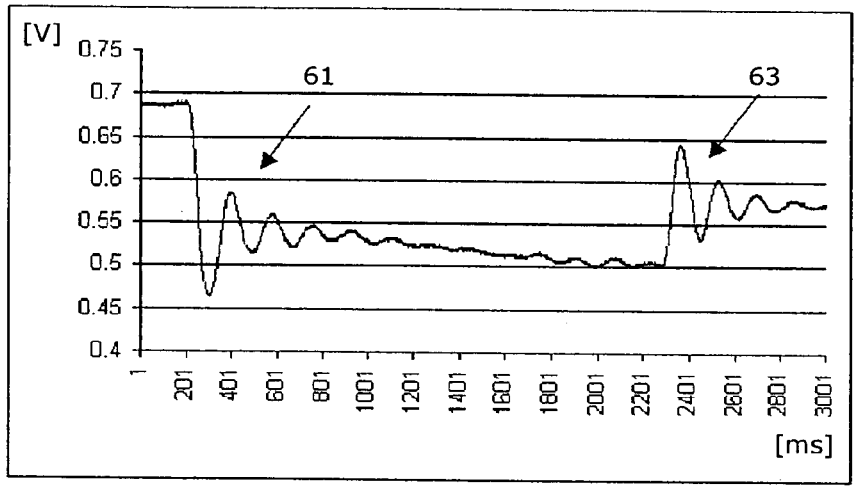
FIG. 14 the substantially continuous system liquid column of the pipetting apparatus has characteristic oscillation frequencies, which can be monitored with the implemented pressure transducer and pressure sensor.

First, only pressure measurement was started (60) with the pipette tip 2 in air (see FIG. 13). While the tip 2 of channel IV being in air (60), but close to the liquid surface as detected before, slow aspiration (200 pump steps per second=66 µl per second) and a downward movement of the tip was started (61) with the Z-rod of a robotic sample processor (RSP) to which the pipetting apparatus 1 of channel IV was attached. No change of pressure was recorded at that time. Then, the pipette tip 2 of channel IV was moved to the liquid surface 17 and—by penetrating the liquid surface 17 (62), aspiration of liquid started immediately and a significant pressure drop was recorded. The time allowed for this aspiration was 40 ms with the 200-µl pipette tip. After this time, the pump piston 18 was brought to a full stop (63). This abrupt stopping the pump piston 18, and therefore also the system liquid column 10, a characteristic pressure oscillation was recognized (64). This oscillation results from the mass moment of inertia of the system liquid column 10 in the fluidic space 7 of the pipetting apparatus 1.

The pipette tip 2 of channel IV was then retracted by 30 steps (65) and the dilutor was set to position zero. This resulted in a dispensation (66-67) of the previously aspirated liquid and air volumes. If a bubble at the pipette tip orifice 3 is produced by such a dispense, this is detectable as a distinct pressure peak (67) at the time of breaking of the bubble. If only a braking liquid film is formed at the pipette tip orifice 3, this is recorded as a plateau (68) instead of the peak; sometimes both phenomena occur as seen in FIG. 13. Falling of the recoded pressure to approximately the same level (69) as initially recorded (60) proves that the pipette tip 2 was completely emptied by this dispense. If the pipette tip 2 is empty again, stopping of the pump piston 18 (70) produces no pressure change in the gas filled space 15 of the pipetting apparatus 1. Following this, the RSP arm was moved to a disposal tray and the pipette tip 2 of channel IV was ejected there.

The same procedure was also carried out using standard pipette tips with or without filter; very similar results have been achieved. Also a slower piston speed of only 15 steps/sec or 3 µl/sec revealed similar and reproducible results. However, a higher piston speed is favored in order to increase the over all processing speed. Using this procedure, the approaching speed of the pipette tip orifice 2 towards the liquid surface 17 was 20 mm/sec or 40 mm/sec (see FIG. 13) for pLLD. This is comparable to the standard approaching speed of about 60 mm/sec utilized for standard cLLD.

As earlier pointed out, the impulse generating means 16 according to the FIGS. 7, 8, and 9A-9D are mainly applicable for reciprocal movements of the liquid column 10 inside the fluidic space 7 of the pipetting apparatus 1 as depicted in FIGS. 6A-6D. Such inducing of reciprocal movement is now discussed in view of the second major application of the pressure variation in the gas filled space 15, the detection of gas bubbles in the system liquid 8 contained in the fluidic space 7.

Gas or air, usually present as bubbles in the system liquid 8, would affect pipetting precision and accuracy in an intolerable way. Such gas bubbles however, are often not visible for an operator of a robotic sample processor for liquid handling. On the one hand, these gas bubbles are too small or, on the other hand, they appear on hidden positions. Up today, it was only possible to detect the presence and effect of such gas bubbles by an extended and costly gravimetric quality control.

The liquid system, i.e., the substantially continuous system liquid column 10 of the pipetting apparatus 1 according to the present invention, has characteristic oscillation frequencies, which can be monitored with the implemented pressure transducer 11 and pressure sensor 12 (see FIG. 14): The correct working system has very little or no gas bubbles in the system liquid 8. This makes the system liquid column 10 to be rigid and capable to oscillate with a high frequency. The typical frequency is similar at the beginning (61) and at the end of every movement the system liquid column 10 is carrying out (63). Thus, at the start and at the end of every aspiration or dispense procedure, the characteristic oscillation frequency of the system liquid column 10 can be detected with the pressure sensor 12 in the gas filled space 15 of the pipetting apparatus 1 of the present invention. If one compares this pressure oscillation at the end of the aspiration (63), with the pressure oscillation (64) after the full stop (63) of the plunger in FIG. 13, the similarity of the oscillation graph is obvious.

Figure 15A:
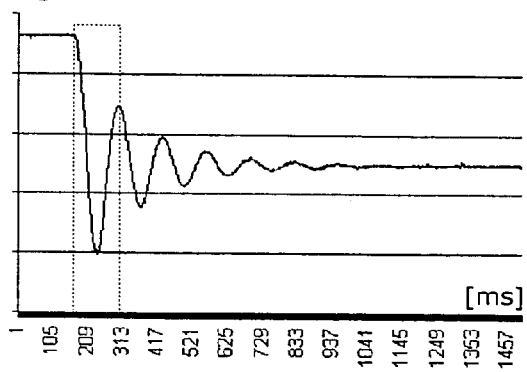
FIG. 15A the absence.
Figure 15B:
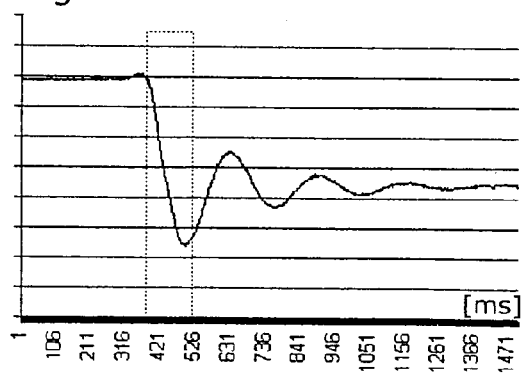
FIG. 15B the presence of gas or air bubbles in the system liquid.

System oscillations, preferably as produced with the electrically controlled impulse generation means 16 of the present invention, are correlated with the absence (see FIG. 15A) or the presence (see FIG. 15B) of gas or air bubbles in the system liquid 8. Frequency limits can be evaluated in order to determine the tolerable amount of gas bubbles in the system liquid 8, which still allows a reasonably precise pipetting to be carried out. No gravimetric quality control is then necessary anymore. As can be seen from FIG. 15B, gas bubbles present in the system liquid 8 turns the system to become softer with a decreased oscillation frequency. Thus, a system with an oscillation as shown in FIG. 15A, can pass the gravimetric quality control; a system producing an oscillation behavior like it is shown in FIG. 15B, will not pass that quality control. For an easier comparison of the graphs in FIG. 15, a similar time window (dashed) is drawn. As estimated from this graphs, the oscillation frequency demonstrated for present gas bubbles is about half the frequency of the bubble free system The method of detecting the presence of gas bubbles in the system liquid 8 of a pipetting apparatus 1 according to the present invention comprises the steps of:

(a) Filling the fluidic space 7 at least partially with a system liquid 8 and forming a substantially continuous system liquid column 10 within the fluidic space 7;

(b) Inducing a vertical movement in this system liquid column 10 by an impulse generating means 16, 18, 19 that is in operative contact with the system liquid column 10, thereby causing a pressure variation in the gas filled space 15 that is pneumatically connected with the fluidic space 7;

(c) Recording the pressure variation in the gas filled space 15 with the pressure transducer 11 and processing the recorded data with a first data processing unit 13; and (d) Deciding according to the processed data, whether gas bubbles are present in the system liquid 8 that is within the fluidic space 7.

Advantages of this method comprise:

The liquid handling system is permanently controlled in terms of quality of performance, whereas the known gravimetric quality control provides only momentary information;

Due to the on-line control, pipetting errors caused by gas bubbles in the system liquid 8 can be prevented.

What is claimed is:

1. Liquid level detection method for a pipetting apparatus (1) that comprises a fluidic space (7), to which a pressure transducer (11) is attached with a gas filled space (15); the fluidic space (7) being defined by a pipette tip (2), a first tubing (5) that connects the pipette tip (2) to a pump (4), and an active part (6) of the pump (4); wherein the liquid level detection method comprises the steps of:

(a) filling the fluidic space (7) at least partially with a system liquid (8) and forming a substantially continuous system liquid column (10) within the fluidic space (7);
(b) inducing a vertical movement in this system liquid column (10) by an impulse generating means (16, 18, 19) that is in operative contact with the system liquid column (10), thereby causing a pressure variation in the gas filled space (15) that is pneumatically connected with the fluidic space (7);
(c) recording the pressure variation in the gas filled space (15) with the pressure transducer (11) and processing the recorded data with a first data processing unit (13); and
(d) deciding according to the processed data, whether a liquid surface (17) had been penetrated or quitted with an orifice (4) of the pipette tip (2).

2. The method of claim 1, wherein the pressure variation—as recorded with the pressure transducer (11) and as processed by a first data processing unit (13) according to step (c)—is indicative for the presence or absence of a filter in the pipette tip (2).

3. The method of claim 1, wherein the decision according to step (d) is carried out on the base of a pressure oscillation frequency recorded by the pressure transducer (11) during an initial or final part of an aspiration process.

4. The method of claim 1, wherein vertically moving this system liquid column (10) in step (b) is a discontinuous or continuous bidirectional oscillation movement, caused by oscillation of a piston (18) or of bellows of the pump (4), or caused by oscillation of a membrane (20, 42) that is part of the pump (4) or of a constriction element (19).

5. The method of claim 4, wherein discontinuous oscillating, single pulsing, or single stepping this system liquid column (10) according to step (b) is carried out in between of two steps of moving the pipette tip orifice (4) towards the liquid surface (17).

6. The method of claim 4, wherein continuous oscillating, repeated pulsing, or repeated stepping this system liquid column (10) of step (b) is carried out during movement of the pipette tip orifice (4) towards the liquid surface (17).

7. The method of claim 1, wherein vertically moving this system liquid column (10) in step (b) is a single or repeated bidirectional pulse movement caused by impulses carried out with a piston (18) or with bellows of the pump (4), or caused by impulses carried out with a membrane (20, 42) that is part of the piston (18) or of a constriction element (19).

8. The method of claim 1, wherein vertically moving this system liquid column (10) in step (b) is a single or repeated unidirectional downward or upward step movement caused by a single or repeated forward or backward movement of a piston (18) or of bellows of the pump (4).

9. The method according to claim 1 for the aspiration and dispensation of volumes of liquids.

10. Bubble detection method for a pipetting apparatus (1) that comprises a fluidic space (7) to which a pressure transducer (11) is attached with a gas filled space (15); the fluidic space (7) being defined by a pipette tip (2), a first tubing (5) that connects the pipette tip (2) to a pump (4), and an active part (6) of the pump (4); wherein the bubble detection method comprises the steps of:
(a) filling the fluidic space (7) at least partially with a system liquid (8) and forming a substantially continuous system liquid column (10) within the fluidic space (7);
(b) inducing a vertical movement in this system liquid column (10) by an impulse generating means (16, 18, 19) that is in operative contact with the system liquid column (10), thereby causing a pressure variation in the gas filled space (15) that is pneumatically connected with the fluidic space (7);
(c) recording the pressure variation in the gas filled space (15) with the pressure transducer (11) and processing the recorded data with a first data processing unit (13); and
(d) deciding according to the processed data, whether gas bubbles are present in the system liquid (8) that is within the fluidic space (7).

11. The method according to claim 10 for the aspiration and dispensation of volumes of liquids.

12. The method of claim 10, wherein the decision according to step (d) is carried out on the base of a pressure oscillation frequency recorded by the pressure transducer (11) during an initial or final part of an aspiration process.

* * * * *